US00PP11516P

United States Patent [19]

Reiner et al.

[11] Patent Number: Plant 11,516

[45] Date of Patent: Sep. 26, 2000

[54] PETUNIA PLANT NAMED 'ROYAL FROST'

[75] Inventors: Kevin M. Reiner, Mt. Vernon; Mary H. Dodsworth, Newark, both of Ohio

[73] Assignee: Timbuk Farms, Inc., Granville, Ohio

[21] Appl. No.: 09/105,365

[22] Filed: Jun. 26, 1998

[51] Int. Cl.[7] ..... A01H 5/00

[52] U.S. Cl. ..... Plt./356

[58] Field of Search ..... Plt./356

[56] References Cited

U.S. PATENT DOCUMENTS

P.P. 10,086 10/1997 Rother ..... Plt./356

*Primary Examiner*—Howard J. Locker
*Assistant Examiner*—Wendy A. Baker
*Attorney, Agent, or Firm*—C. A. Whealy

[57] ABSTRACT

A distinct cultivar of Petunia plant named 'Royal Frost', characterized by its bright purple flowers; cascading and freely branching growth habit; and unique green and very light yellow variegated foliage.

2 Drawing Sheets

BACKGROUND OF THE INVENTION

The present invention relates to a new and distinct cultivar of Petunia plant, botanically known as *Petunia axillaris*, and hereinafter referred to by the cultivar name Royal Frost.

The new Petunia is a naturally-occuring mutation of *Petunia axillaris* cultivar Purple Wave (not patented). The new Petunia was discovered and selected by the Inventors in April, 1997, as a flowering plant within a population of plants of the cultivar Purple Wave grown in a controlled environment in Granville, Ohio. The new Petunia was selected on the basis of its unique variegated foliage.

Asexual reproduction of the new cultivar by terminal cuttings taken at Granville, Ohio, has shown that the unique features of this new Petunia are stable and reproduced true to type in successive generations.

SUMMARY OF THE INVENTION

Plants of the cultivar Royal Frost have not been observed under all possible environmental conditions. The phenotype may vary somewhat with variations in environment such as temperature, light intensity, daylength, and fertility level without, however, any variance in genotype. The following observations, measurements and comparisons describe plants grown in Granville, Ohio, under commercial production conditions.

The following traits have been repeatedly observed and are determined to be the unique characteristics of 'Royal Frost'. These characteristics in combination distinguish 'Royal Frost' as a new and distinct cultivar:

1. Bright purple flowers.
2. Cascading and freely branching growth habit.
3. Unique green and very light yellow variegated foliage.

Plants of the cultivar Royal Frost are similar in flower color to plants of the parent cultivar Purple Wave. However in side-by-side comparisons conducted by the Inventors in Granville, Ohio, plants of the cultivar Royal Frost differ from plants of the cultivar Purple Wave in the following characteristics:

1. Plants of the new Petunia are smaller and have shorter internodes than plants of the cultivar Purple Wave.
2. Plants of the new Petunia are less vigorous and slower growing than plants of the cultivar Purple Wave.
3. Flowers and leaves of the new Petunia are smaller than flowers and leaves of the cultivar Purple Wave.

4. Plants of the new Petunia have fewer flowers than plants of the cultivar Purple Wave.
5. Plants of the new Petunia have variegated foliage whereas plants of the cultivar Purple Wave have solid green leaves.

A detailed comparison of plants of the new Petunia and the cultivar Purple Wave appears in Chart A at the end of the specification.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical hanging basket plant of the new Petunia.

The photograph on the second sheet comprises a close-up view of typical flowers and leaves of the new Petunia Royal Frost. Flower and foliage colors in the photographs may appear different than the actual colors due to light reflectance.

DETAILED BOTANICAL DESCRIPTION

In the following description, color references are made to The Royal Horticultural Society Colour Chart except where general terms of ordinary dictionary significance are used. Plants used for the description were grown in greenhouses under typical production conditions in 25—cm hanging baskets during the late spring in Granville, Ohio.

Botanical classification: *Petunia axillaris* cultivar Royal Frost.

Parentage: Naturally-occurring mutation of *Petunia axillaris* cultivar Purple Wave (not patented).

Propagation:

*Type cutting.*—Terminal vegetative cuttings.

*Time to initiate and develop roots.*—About 10 to 14 days at 20° C. soil temperature.

*Rooting habit.*—Numerous, fine, fibrous, and well-branched.

Plant description:

*Form.*—Indeterminate, decumbent, cascading, viscid, glandular pubescent.

*Branching habit.*—Freely branching, lateral branches typically form at every node.

*Plant height (from soil level to top of plant plane).*—About 8 cm.

*Spreading area of plant.*—About 42 cm, cascading.

*Vigor.*—Low to moderate.

*Foliage description.*—Leaves simple, generally symmetrical and long persisting. Leaves usually opposite, somewhat fleshy, glandular. Length: About 3.75 cm. Width: About 2.3 cm. Thickness: About 0.75 mm. Aspect: Horizontal to upward. Shape: Ovate. Apex: Acute. Base: Obtuse. Margin: Entire. Texture: Both surfaces and margins pubescent. Color: Variegated; green centers surrounded by very light yellow. Young foliage upper surface: Center green, 146B/146C to 147B; surrounded by lighter green, 146D, and/or very light yellow, close to 8D. Young foliage lower surface: Center green, 146C to dulled 147B; surrounded by lighter green, 146D, and/or very light yellow, close to 8D. Mature foliage upper surface: Center green, 147B/147C, slightly dulled; surrounded by very light yellow, 8D/11D. Mature foliage lower surface: Center green, dulled 147B; surrounded by very light yellow, 8D/11D. Peduncle: Length: About 7 mm. Diameter: About 2 mm. Texture: Pubescent. Color: 146B.

*Stem description.*—Diameter: About 3 mm. Internode length: About 2.1 cm. Texture: Very pubescent, glandular. Color: Green, 144A.

Flower description:

*Flower type and habit.*—Large, single, salverform flowers, facing upwards, axillary. Calyx five-parted, petals united into a flower tube.

*Natural flowering season.*—Long day responsive, continuously flowers from spring through fall.

*Quantity.*—Numerous flowers per plant.

*Corolla.*—Diameter: About 4.25 cm. Height: About 3.3 cm. Flower tube width at distal end: Narrow, about 7 mm. Petal quantity: Five, fused. Petal apex: Acuminate. Margin: Entire. Texture: Pubescent on lower surface, smooth and satiny on upper surface; iridescent. Color: Flower throat (inside): 82A/83A. Flower throat vein color (inside): 83A. Flower tube color (outside): 83B/83C. Petal color, upper surface: 74A. Petal vein color, upper surface: 83A/83B. Petal color, lower surface: 81A to 81C.

*Sepals.*—Quantity: Five. Length: About 1.3 cm. Width: About 2 mm. Shape: Linear. Apex: Rounded. Margin: Entire. Aspect: Upright. Texture: Pubescent. Color: 144B/144C.

*Peduncle.*—Aspect: Erect, upright. Length: Short, about 1.4 cm. Width: Narrow, about 1 mm. Texture: Pubescent. Color: 144A.

*Reproductive organs.*—Stamens: Stamen number: Five. Anther color, before dehiscence: 93D. Filament color: Greenish white, violet towards anthers. Pollen color: 96B. Pistils: Stigma color: 144B. Style color: Greenish white.

Disease resistance: No resistance to diseases common to Petunia has been observed.

Seed production: Seed production has not been observed.

CHART A

| CHARACTERISTIC | 'ROYAL FROST' | 'PURPLE WAVE' |
|---|---|---|
| LEAF LENGTH | About 3.75 cm | About 4.8 cm |
| LEAF WIDTH | About 2.3 cm | About 3.1 cm |
| LEAF COLOR, MATURE, UPPER SURFACE | Variegated; center, 147B/147C, slightly dulled; surrounded by very light yellow, 8D/11D | Greener than 147B, no variegation |
| COROLLA DIAMETER | About 4.25 cm | About 5.75 cm |
| COROLLA HEIGHT | About 3.3 cm | About 2.8 cm |
| PETAL COLOR, OPENED, UPPER SURFACE | 74A | 74A |
| PETAL COLOR, OPENED, LOWER SURFACE | 81A to 81C | 81A/81B |

It is claimed:

1. A new and distinct cultivar of Petunia plant named 'Royal Frost', as illustrated and described.

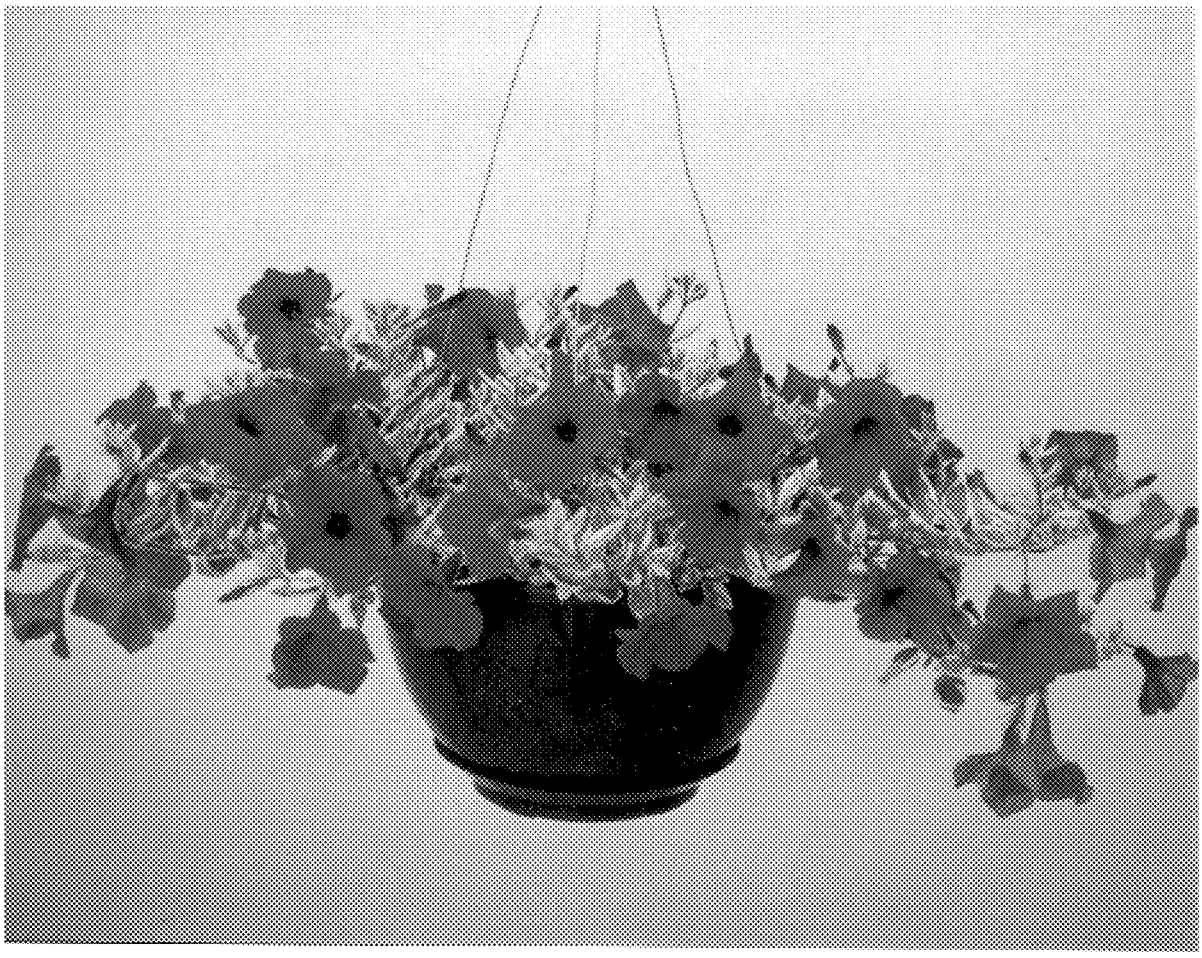

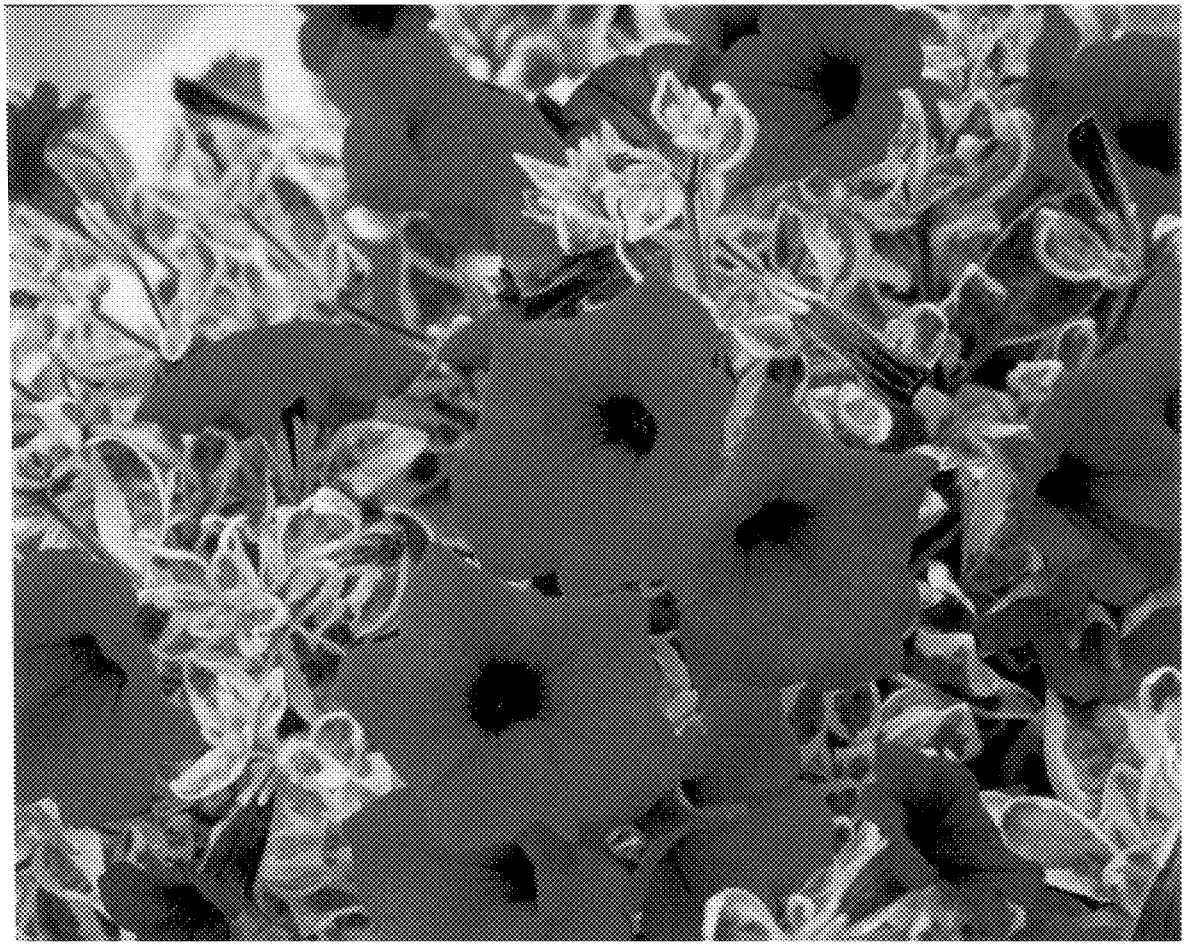

* * * * *